United States Patent [19]

Hubele

[11] 3,941,832

[45] Mar. 2, 1976

[54] OXIME ETHERS AND PESTICIDAL PREPARATIONS CONTAINING THEM

[75] Inventor: Adolf Hubele, Riehen, Switzerland

[73] Assignee: Ciba-Geigy AG, Basel, Switzerland

[22] Filed: Jan. 23, 1975

[21] Appl. No.: 543,582

Related U.S. Application Data

[60] Division of Ser. No. 339,247, March 8, 1973, Pat. No. 3,876,697, which is a division of Ser. No. 46,832, June 16, 1970, Pat. No. 3,733,359, which is a continuation-in-part of Ser. No. 521,413, Jan. 18, 1966, abandoned.

[30] Foreign Application Priority Data

Jan. 22, 1965 Switzerland............ 915/65
July 9, 1965 Switzerland............ 9630/65

[52] U.S. Cl................................. 260/471 R
[51] Int. Cl.²............................... C07C 101/00
[58] Field of Search............... 260/471 R, 566 AE

[56] References Cited
UNITED STATES PATENTS 2,712,031  6/1955  Huffman................. 260/566 AE
3,577,441  5/1971  Kaminsky et al........... 260/566 AE

FOREIGN PATENTS OR APPLICATIONS 1,096,037  12/1967  United Kingdom......... 260/566 AE

OTHER PUBLICATIONS

Beilstein's Handbuch der Organischen Chemie, Vol. VII, p. 895, (1968); Vol. III, pp. 236–237, (1969).

*Primary Examiner*—Gerald A. Schwartz
*Attorney, Agent, or Firm*—Frederick H. Rabin

[57] ABSTRACT

New oxime ethers and pesticidal and herbicidal preparations containing them are disclosed. The oxime ethers correspond to the formula

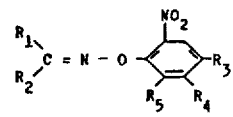

wherein $R_1$ is a hydrogen atom or a lower alkyl radical; $R_2$ is an aliphatic, cycloaliphatic, araliphatic, aromatic or heterocyclic radical; or wherein $R_1$ and $R_2$ form part of a saturated or unsaturated carbocycle or a 5-, 6- or 7-membered heterocycle; $R_3$ is nitro, trifluoromethyl, formyl, lower carbalkoxy, sulfamyl or mono- or di-lower alkyl fulfamyl radical; $R_4$ and $R_5$ each is a hydrogen or halogen atom, an amino, mono- or di-lower alkyl amino, lower alkoxy, cycloalkoxy, lower alkylthio, nitro, lower carbalkoxy, arylthio, lower aralkylthio or lower alkyl group, or 5-, 6- or 7-membered heterocycle.

1 Claim, No Drawings

OXIME ETHERS AND PESTICIDAL PREPARATIONS CONTAINING THEM

BACKGROUND OF THE INVENTION

The present invention provides new oxime ethers and pesticidal preparations containing them. The oxime ethers correspond to the formula

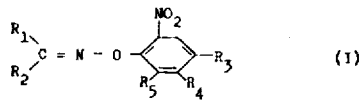

wherein $R_1$ is a hydrogen atom or a lower alkyl radical; $R_2$ is an aliphatic, cycloaliphatic, araliphatic, aromatic or heterocyclic radical; or wherein $R_1$ and $R_2$ form part of a saturated or unsaturated carbocycle or a 5-,6-or 7-membered heterocycle; $R_3$ is a nitro, trifluoromethyl, formyl, lower carbalkoxy, sulfamyl or mono- or di- lower alkylsulfamyl radical; $R_4$ and $R_5$ each is a hydrogen or halogen atom, an amino, mono- or dilower alkylamino, lower alkoxy, cycloalkoxy, lower alkylthio, nitro, lower carbalkoxy, arylthio, lower aralkylthio group or 5-, 6- or 7-membered heterocycle.

$R_1$ in the above formula stands for a lower alkyl radical. Such radicals contain 1 to 4 carbon atoms and may be branched or unbranched such as the methyl and ethyl groups or the normal or iso-propyl or butyl group or secondary or tertiary butyl group. Preferred groups, however, are besides the hydrogen atom the methyl and ethyl radicals.

$R_2$ stands for an aliphatic, cycloaliphatic, araliphatic, aromatic or heterocyclic radical. The aliphatic radical may be branched or unbranched, saturated or unsaturated. Preferably such radicals contain up to 8 carbon atoms and are alkyl or alkenyl radicals which may be substituted or unsubstituted. Suitable substituents are for instance halogen atoms, such as fluorine, chlorine or bromine or hydroxy or alkoxy groups. The cycloaliphatic radicals contain 3 to 8 carbon atoms and may be saturated or unsaturated and mono- or polycyclic. As a rule they contain 3 to 12 carbon atoms and are saturated. They preferably are mono- or bicyclic and have 3 to 7 ring members. The araliphatic radicals contain in the aromatic moiety at least one benzene nucleus and in the aliphatic moiety preferably an unbranches chain containing 1 to 4 carbon atoms. This aliphatic chain may be saturated or unsaturated, substituted or unsubstituted. Suitable substituents are hydroxy groups and halogen atoms, such as chlorine and especially bromine. Suitable chains contain 2 carbon atoms and are saturated; they may also contain one or two bromine atoms or one double bond. Aromatic radicals are to be understood as being substituted or unsubstituted phenyl radicals or condensed ring systems. The preferred embodiment are substituted and unsubstituted phenyl radicals. Suitable substituents on the phenyl moiety are e.g. halogen atoms such as fluorine and especially chlorine, bromine and iodine; lower alkyl and alkoxy groups containing 1 to 4 carbon atoms; hydroxy groups; amino groups which may be substituted by one or two lower alkyl, lower alkoxyalkyl or lower alkanol radicals; nitro groups; lower alkyl carbamoyl radicals; phenoxy groups which may be substituted by one or more of the substituents enumerated above for the phenyl radical especially by nitro groups. The heterocyclic radicals coming into consideration particularly are 5- or 6-membered and contain at least one oxygen or sulfur especially however nitrogen atom. These heterocycles may be substituted, preferably by lower alkyl radicals, especially the methyl group. Examples of such heterocycles are i.a. pyridine and quinaldine compounds.

$R_3$ stands for a trifluoromethyl, formyl, nitro, lower carbalkoxy, sulfamyl or mono- or di-lower alkysulfamyl group. The alkyl moieties of the carbalkoxy and alkylsulfamyl group contain 1 to 4 carbon atoms and may be branched or unbranched. Preferred alky moieties contain 1 or 2 carbon atoms. However, suitable substitutent are not limited to the above enumeration. Thus also halogenalkyl groups quite generally may be used. Moreover, halogen atoms such as chlorine, bromine and iodine; alkyl groups containing 1 to 6 carbon atoms, the carboxyl group; lower alkyl- or aryl-, especially phenylcarbamyl groups; the sulfonic acid groups; and lower alkylsulfonyl groups may be used likewise.

$R_4$ and $R_5$ each stands for a hydrogen or halogen atom, a lower alkyl, amino, mono- or di- lower alkylamino, lower alkoxy, cycloalkoxy, lower alkylthio, lower carbalkoxy, arylthio, lower aralkylthio, nitro or heterocyclic radical. The halogen atoms may be elected from fluorine, bromine, iodine and especially chlorine. The lower alkyl moieties enumerated above contain 1 to 4 carbon atoms and may be branched or unbranched. The heterocyclic radicals are 5-, 6- or 7-membered, especially 5- or 6-membered, and contain as hetero- atoms one or more oxygen, sulfur or especially nitrogen atoms. Such heterocyclic radicals are i.a. the pyridino and morpholino radical. The cycloalkoxy radicals are 3 to 8-membered, especially however 6-membered. Representative of such radicals is the cyclohexoxy radical. Especially suitable oxime ethers are those which correspond to the formulae

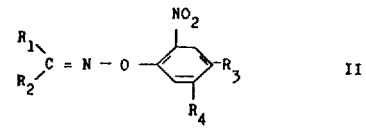

or

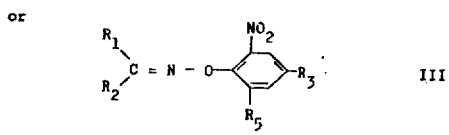

wherein $R_1$, $R_2$, $R_3$, $R_4$ and $R_5$ have the meanings given above. More particularly $R_3$ stands for a nitro, trifluoromethyl, formyl, methylcarbonyl, methylsulfamyl or a dimethylsulfamyl radical. $R_4$ for a hydrogen or chlorine atom, an amino, methyl amino, dimethyl amino, isopropylamino, methoxy, ethoxy, benzylmercapto or morpholino group, and $R_5$ for a hydrogen atom, a methyl, sec.butyl, carbomethoxy, nitro or cyclohexoxy radical.

From among the compounds of formula (III) those should be specially mentioned which correspond to the formulae

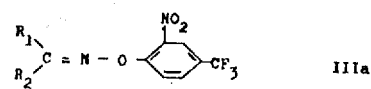

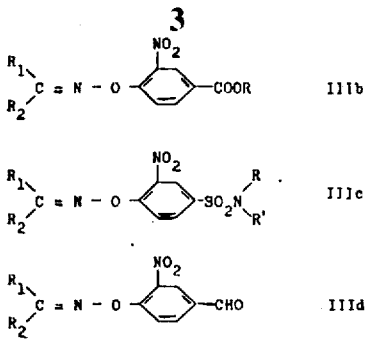

wherein $R_1$ and $R_2$ have the meanings given above and R and R' each is hydrogen, lower alkyl, such as methyl, ethyl, propyl, isopropyl, butyl, isobutyl, sec.butyl, tert.butyl amyl or cycloalkyl, such as cyclopentyl or cyclohexyl.

From among the compounds of formulae (II) and (III) those are preferred which correspond to the formula

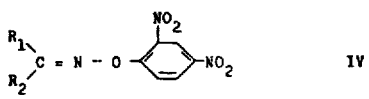

wherein $R_1$ and $R_2$ have the above meanings. More particularly $R_1$ may stand for hydrogen and $R_2$ for a substituted phenyl radical. Such compounds correspond to the formulae

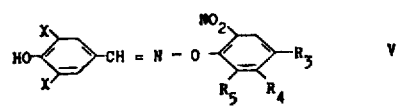

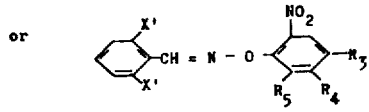

and more specifically to the formulae

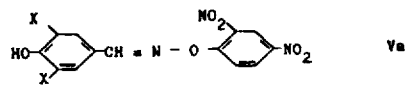

or

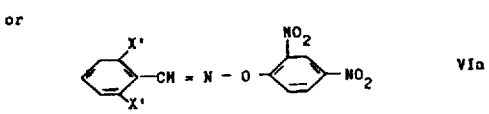

wherein $R_3$, $R_4$ and $R_5$ have the meanings given above and X and X' each stands for halogen. More specifically X represents chlorine bromine and iodine, whereas X' stands for chlorine.

The oxime ethers of the formulae (I) to (VI) may be derived from aliphatic, araliphatic, aromatic or heterocyclic aldehydes or ketones, and also from quinones and endocyclic ketones for example fluorenone, indanone, acenaphthenone, anthrone, N-methylpyridone, N-methylpiperidone, furfurol or nitrofurfurol.

Preferred use is made of oxime ethers derived from aliphatic aldehydes or ketones, from araliphatic aldehydes or ketones, or from aromatic or heterocyclic aldehydes or ketones.

Suitable aliphatic aldehydes are simply constituted aldehydes for example acetaldehyde, propionaldehyde, butyraldehyde or aldehydes having a longer chain, for example heptaldehyde, stearaldehyde or unsaturated aldehydes for example crotonaldehyde. Suitable aliphatic ketones are simple ketones for example acetone, methylethyl ketone, hexanone-(3), diisopropylketone, mesityl oxide, and phorone. Suitable araliphatic or aromatic aldehydes and ketones are cinnamic aldehyde, hydrocinnamic aldehyde, halogen adducts or cinnamic aldehyde for example dibromo-cinnamic aldehyde, diiodo-cinnamic aldehyde, acetophenone, propiophenone, benzaldehyde, nuclear halogenated, alkylated, nitrated and alkoxylated benzaldeyhdes. Examples of suitable cyclic ketones are cyclopentanone, cyclohexanone, cycloheptanone as well as their cyano derivatives. Suitable heterocyclic ketones and aldehydes are, for example, picoline aldehyde nicotine aldehyde, isonicotine aldehyde and N-alkylpiperidones.

If such aldehydes or ketones contain aromatic radicals, their suitably substituted derivatives may likewise be used. These substituents may be of a non-functional kind, for example halogen atoms, nitro or nitroso groups, or of a functional kind or derived from functional substituents, being, for example hydroxyl, acyloxy, carbamoyloxy, alkoxy, aryloxy, thiol, acylthio, alkylthio, trifluoromethyl, cyano, formyl, amino, alkylamino, dialkylamino, arylamino, diarylamino, carboxy or carbalkoxy groups.

By virtue of their broad biocidal spectrum the new oxime ethers offer the special advantage that they are suitable for combating a very wide variety of vegetable and animal pests. They are suitable not only for use as herbicides, which is the preferred utility, but when used in a concentration that does not produce any phytotoxic effects, they are very useful in plant protection for combating harmful micro-organisms, such as phytopathogenic fungi, for example Altérnaria solani, Phytophthora infestans and Septoria apii, and act also against harmful insects, acarides, nematodes and their ova and larvae. They may also be used quite generally as microbicides, for example against Aspergillus species, and as insecticides, for example against midges and flies.

The oxime ethers according to this invention may be used per se or in admixture with suitable carriers. Such carriers may be solid or liquid. The pesticidal preparations thus formed may therefore contain a solid carrier, a solvent diluent, dispersant, wetting agent, adhesive, fertilizer and/or other known pesticides.

For the manufacture of solutions of compounds of the general formula (I) for direct spraying there may be used, for example, petroleum fractions of a high to medium boiling range, for example Diesel oil or kerosene, coal tar oil and oils of a vegetable or animal origin, as well as hydrocarbons for example alkylated naphthalenes, tetrahydronaphthalene if desired in conjunction or admixture with xylene mixtures, cyclohexanels, ketones, chlorinated hydrocarbons for example trichloroethane or tetrachloroethane, trichlorethylene, tri- or tetrachlorobenzene. It is advantageous to use organic solvents boiling above 100°C.

Aqueous forms of applications are prepared most advantageously from emulsion concentrates, pastes or wettable spray powders by addition of water. Suitable emulsifying or dispersing agents are non-ionic products, for example condensation products of aliphatic alcohols, amines or carboxylic acids containing a long-chain hydrocarbon residue of about 10 to 20 carbon atoms with ethylene oxide, for example the condensation product of octadecyl alcohol with 25 to 30 mols of ethylene oxide, or of soybean fatty acid with 30 mols of ethylene oxide, or of commercial oleylamine with 15 mols of ethylene oxide, or of dodecylmercaptan with 12 mols of ethylene oxide. From among suitable anionic emulsifiers, there may be mentioned the sodium salt of dodecyl alcohol sulphuric acid ester, the sodium salt of dodecylbenzenesulphonic acid, the potassium or triethanolamine salt of oleic or abietic acid or of mixtures of these acids, or the sodium salt of a petroleum-sulphonic acid. Suitable cationic dispersants are quaternary ammonium compounds, for example cetyl pyridinium bromide or dihydroxyethyl benzyl dodecyl ammonium chloride.

For the manufacture of dusting and casting preparations, there may be used as solid vehicles talcum, kaolin, bentonite, calcium carbonate, calcium phosphate, or coal, cork meal, wood meal or other materials of vegetable origin. It is also very advantageous to manufacture preparations in granular form. The various forms of application may contain the usual additives for improving the distribution, the adhesion, the stability towards rain or the penetration; as such substances there may be mentioned fatty acids, resin, glue, casein and alginates.

The preparations of this invention may be used by themselves or in conjunction or admixture with conventional pesticides, especially insecticides, acaricides, nematocides, bactericides or further fungicides or herbicides.

Especially potent herbicides are those preparations which contain as active ingredient a compound of the formula

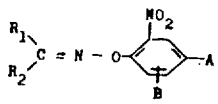

Ia wherein $R_1$ represents a hydrogen atom or an aliphatic radical and $R_2$ an aliphatic radical or an unsubstituted or substituted phenyl group, A represents —$NO_2$, —CHO, —COOH or COO alkyl, and B stands for hydrogen, —$NO_2$, —COOH, —COOalkyl or chlorine. The phenyl radical $R_2$ may carry various substituents, for example halogen atoms, nitro, alkyl, hydroxyl or alkoxy groups and/or carbamoyloxy groups.

Particularly potent herbicides are the compounds of the formula (Ia) wherein $R_1$ and $R_2$ have the following meanings:

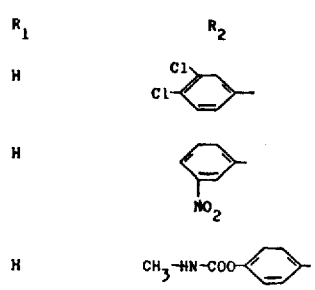

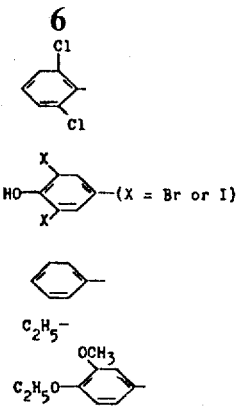

Especially useful acaricides are those preparations which contain as active ingredient a compound of the formula

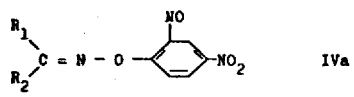

IVa wherein $R_1$ represents a hydrogen atom and $R_2$ a phenyl radical which may be substituted by halogen atoms or alkyl or alkoxy groups, or wherein $R_1$ and $R_2$ represent alkyl radicals or are part of an isocyclic residue.

Especially potent are the compounds of the formula

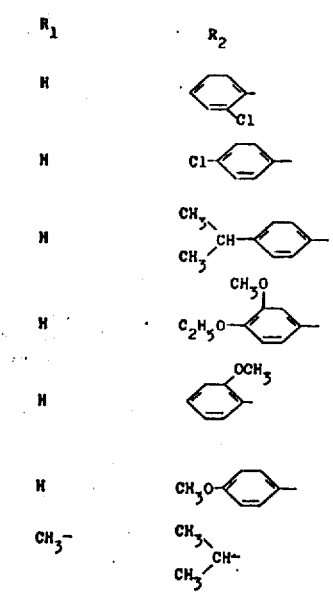

The active ingredients of formula I may be manufactured according to known methods, such as e.g.:

A salt of a ketoxime or aldoxime of the formula

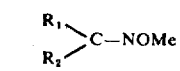

wherein $R_1$ and $R_2$ have the above meanings and Me stands for a metal atom, preferably an alkali metal atom- is reacted with a halogeno-benzene of the formula

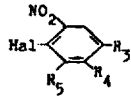

wherein $R_3$ to $R_5$ have the above meanings and Hal represents a fluorine, chlorine, bromine or iodine atom.

The reaction may be carried out in a solvent, for example in ethanol, methanol, acetonitrile or dioxan, as a rule at room temperature; in many cases it is accompanied by a spontaneous rise in temperature. The oxime ethers obtained in this manner are very easy to isolate by diluting the reaction solution with water. The ethers precipitate and may, if desired, be recrystallized. This process may be varied in that following upon the formation of the oxime ether one or several groups, $R_3$, $R_4$, $R_5$, $R_6$ are subsequently converted.

More especially, halogen atoms $R_5$ and/or $R_6$ may be exchanged for compounds containing active hydrogen atoms, thus for example for ammonia, primary or secondary aliphatic, araliphatic or aromatic amines, alcohols, phenols, alkanethiols or thiophenols.

The oxime ethers accessible in this manner may take the syn-form or the anti-form. As a rule, they are obtained in the form of a mixture of isomers, which can be resolved into the two forms by a usual operation, for example crystallization or adsorption. For the manufacture of the preparations of this invention, it suffices to use the mixture of isomers as obtained by the reaction.

The present invention further includes new oxime ethers of the general formula

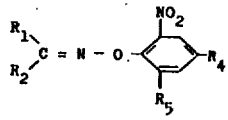

wherein $R_1$ and $R_2$ have the above meanings and $R_4$ represents a trifluoromethyl, formyl, unsubstituted or substituted carboxyl or possibly alkylated sulphamyl residue, and $R_5$ represents a hydrogen atom or a nitro group, or wherein $R_4$ stands for the nitro group and $R_5$ for a possible esterified carboxyl group.

The following Examples illustrate the invention:

EXAMPLE 1

(1) 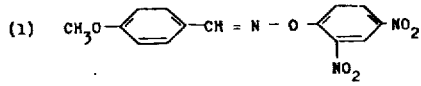

A solution of sodium ethylate prepared from 11.5 parts of sodium and 500 parts by volume of absolute ethanol is added to 76 parts of anisaldehyde in 400 parts by volume of absolute ethanol. During 10 minutes at 40°C 101 parts of 4-chloro-1,3-dinitrobenzene in 300 parts by volume of absolute ehtanol are added drop, the temperature rising to 65°C. The batch is cooled to room temperature, diluted with water, filtered and recrystallized from dimethylformamide-ethanol. The product melts at 187°– 17.5°C.

EXAMPLE 2

(2) 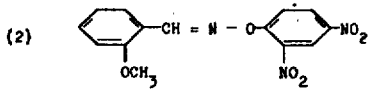

A solution of sodium ethylate prepared from 13.1 parts of sodium and 300 parts by volume of absolute ethanol is added drop by drop during 30 minutes, at room temperature, to a solution of 82 parts of ortho-methoxybenzaldehydeoxime and 115 parts of 4-chloro-1,3-dinitrobenzene in 1000 parts by volume of acetonitrile. After 4 hours, the batch is diluted with 3000 parts by volume of water, filtered and recrystallized from toluene-acetone. The product melts at 184° – 184.5°C.

EXAMPLE 3

(3) 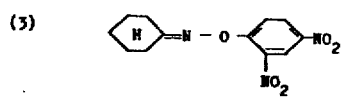

A solution of sodium ethylate prepared from 18.5 parts of sodium and 500 parts by volume of absolute ethanol is added drop by drop during 30 minutes at room temperature to a solution of 90 parts of cyclohexanone oxime and 162 parts of 4-chloro-1,3-dinitrobenzene in 500 parts by volume of acetonitrile. After 4 hours, the batch is diluted with water filtered and recyrstallized from acetonitrile. The product melts at 105.5°–106°C.

EXAMPLE 4

(4) 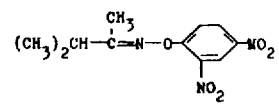

A solution of sodium ethylate prepared from 12 parts of sodium and 250 parts by volume of absolute ethanol is added drop by drop at room temperature to a solution of 50.5 parts of methyl-isopropoyl ketonoxime and 101.3 parts of 4-chloro-1,3-dinitrobenzene in 400 parts by volume of acetonitrile, while stirring. After 12 hours, the batch is diluted with water, filtered and recrystallized from acetonitrile. The product melts at 85° to 86°C.

EXAMPLE 5

(5) 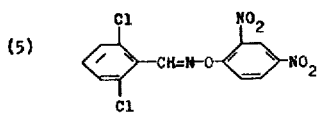

An oxime salt solution of 380 parts of 2.6-dichlorobenzaldehyde oxime, 46.3 parts of soidum in 4000 parts by volume of absolute ethanol is added drop by drop during 1 hour to a cooled mixture of 405 parts of 4-chloro-1,3-dinitrobenzene and 500 parts by volume of acetonitrile while stirring and at a rate such that the temperature remains between −5°C and +10°C. After 3 hours, the batch is diluted with ice water, filtered and recrystallized from dimethylformamide-acetonitrile. The product melts at 177° to 178°C.

EXAMPLE 6

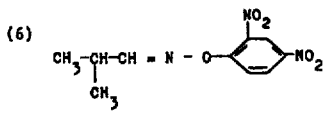

An oxime salt solution of 43.5 parts of isobutyraldoxime and 10.5 parts of sodium in 300 parts by volume of absolute ethanol is added drop by drop during 30 minutes at −5°C to a mixture of 93 parts of 4-fluoro-1,3-dinitrobenzene and 200 parts by volume of acetonitrile, while stirring. The batch is then stirred for 3 hours at room temperature, diluted with ice water, filtered and recrystallized from acetonitrile. The product melts at 80° to 82°C.

EXAMPLE 7

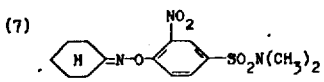

A solution of 54 parts of the cyclohexanone oxime sodium salt in 800 parts by volume of dioxane is added drop by drop at room temperature during 30 minutes to a mixture of 106 parts of 4-chloro-3-nitrobenzenesulphonic acid-(1)-dimethylamide in 500 parts by volume of dioxan while stirring. During the addition, the temperature rises to 35°C. After 2 hours, the batch is heated for ½ hour at 50°C, than diluted with ice water, filtered, and recrystallized from ethanol. The product melts at 124° to 125°C.

EXAMPLE 8

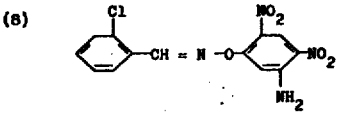

An oxime salt solution prepared from 30 parts of 2-chlorobenzaldehyde oxime, 4.5 parts of sodium and 400 parts by volume of absolute ethanol is added drop by drop at room temperature, during 30 minutes, to a solution of 42 parts of 5-chloro-2,4-dinitraniline in 500 parts by volume of acetonitrile while stirring. After 6 hours, the whole is diluted with ice water, filtered and recrystallized from acetonitrile. The product melts at 166° to 167°C.

EXAMPLE 9

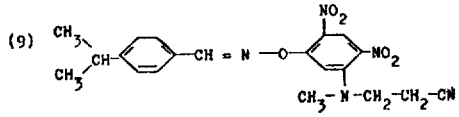

33 Parts of α-methylaminopropionitrile in 200 parts by volume of dioxan are added drop by drop within 1 hour at 50°C while stirring to 69 parts of couminaldehyde oxime-o-(5-chloro-2,4-dinitro-phenyl ether) in 700 parts by volume of dioxan, during which the temperature of the solution rises slightly.

After 1 hour, the batch is diluted with ice water, filtered and recrystallized from ethanol-dimethylformamide. The product melts at 161° to 162°C.

EXAMPLE 10

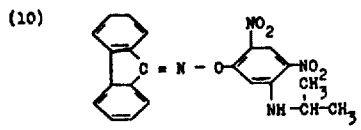

23 Parts of isopropylamine in 100 parts of dioxan are added drop by drop during 1 hour, at 50°C, to 77 parts of fluorenone oxime-o-(5-chloro-2,4-dinitrophenyl ether) in 1500 parts by volume of dioxan. The batch is then refluxed for 3 hours at 80°C, another 20 parts of isopropylamine are added and the mixture is heated for 3 hours at 80°C, diluted with ice water, filtered and digested with hot dimethylformamide. The product melts at 240° to 241°C with decomposition.

EXAMPLE 11

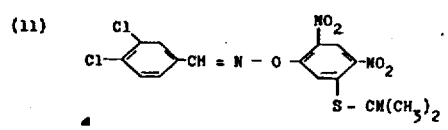

An oxime salt solution prepared from 86 parts of 3,4-dichlorobenzaldoxime, 10.3 parts of sodium and 600 parts by volume of absolute ethanol is added drop by drop at room temperature within ½ hour to 130 parts of isopropyl-(5-chloro-2,4-dinitrophenyl)-sulphide in 400 parts by volume of acetonitrile, while stirring. After 3 hours, the batch is diluted with ice water, filtered and recrystallized from acetonitrile. The product melts at 191° to 192°C.

EXAMPLE 12

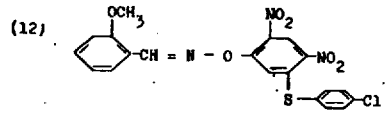

A thiophenolate solution prepared from sodium methylate and 29 parts of 4-chlorothiophenol in 800 parts by volume of dioxan is added drop by drop, under a current of nitrogen, during 30 minutes, to 63 parts of 2-methoxybenzaldehydroxime-O-(5-chloro-2,4-dinitrophenyl ether) in 1000 parts by volume of dioxan, while stirring. The batch is then heated for 1 hour at 40°C, diluted with ice water, filtered and recrystallized from dioxan-dimethylformamide. The product melts at 197° - 198°C.

The following oxime ethers of 2,4-dinitrophenols have been prepared by analogous methods described in the foregoing Examples:

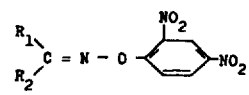

Table 1

| Compound No. | $R_1R_2C=$ | Melting Point °C |
|---|---|---|
| 13 | 2-Cl-C6H4-CH= | 165 – 166 |
| 14 | 4-Cl-C6H4-CH= | 195 – 196 |
| 15 | 3-Cl-C6H4-CH= | 197 – 197.5 |
| 16 | (CH3)2N-C6H4-CH= | 186 – 187 |
| 17 | 2-NO2-C6H4-CH= | 189 – 190.5 |
| 18 | CH3NH-C(O)-O-C6H4-CH= | 181 – 182 |
| 19 | HO-C6H4-CH= | 185 – 186 |
| 20 | 3,5-Cl2-4-OH-C6H2-CH= | 199.5 – 200 |
| 21 | (CH3)2CH-C6H4-CH= | 165 – 166 |
| 22 | O=C6H4= | 164 – 165 |
| 23 | 2-OCH3-4-(2,4-dinitrophenoxy)-C6H3-CH= | 202 – 203 |
| 24 | 2,4-Cl2-C6H3-CH= | 184 – 185 |
| 25 | 3-OCH3-4-(2,4-dinitrophenoxy)-C6H3-CH= | 206.5 – 207 |
| 26 | C6H5-CH= | 142 – 144 |
| 27 | (CH3)2C= | 71 – 71.5 |
| 28 | (C2H5)2N-C6H4-CH= | 141 – 142 |
| 29 | 3-OCH3-4-OC2H5-C6H3-CH= | 143.5 – 144 |
| 30 | 3-OCH3-4-OCH3-C6H3-CH= | 175 – 175.5 |
| 31 | 4-Cl-C6H4-C(CH3)= | 195 – 196 |
| 32 | C6H5-C(CH3)= | 180 – 181 |
| 33 | CH3-(CH2)6-C(CH3)= | yellow oil |
| 34 | 3-NO2-C6H4-C(CH3)= | 198.5 – 199 |
| 35 | 2,4-Cl2-C6H3-C(CH3)= | 200 – 201 (decomp.) |
| 36 | (CH3)2C(CH3)= (tert-butyl) | 89 – 89.5 |
| 37 | 3,5-Br2-4-OH-C6H2-CH= | 196 – 197 |
| 38 | CH3-(CH2)5-C(CH3)= | 47 – 48 |
| 39 | (camphor-like bicyclic)C= | 85 – 97 |
| 40 | (bicyclic terpene)C= | 97 – 111 |
| 41 | 2-Cl-5-NO2-C6H3-CH= | 205 – 206 (decomp.) |
| 42 | (bicyclic)C= | 107 – 109 |
| 43 | 3,5-I2-4-OH-C6H2-CH= | 188 – 190 |

The following oxime ethers of 2,4-dinitro-5-chlorophenol were prepared by methods analogous to those described in the foregoing Examples:

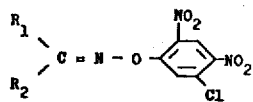

Table 1-continued

| Compound No. | $R_1R_2C=$ | Melting Point °C |
|---|---|---|
| 44 | $(CH_3)_2CH-CH_2$, $(CH_3)_2CH-CH_2$ C= | 75 – 77 |
| 45 | cyclohexylidene ($CH_2-CH_2-CH_2-CH_2-CH_2-CH_2$ ring) C= | 81 – 83 |
| 46 | $C_2H_5$, $C_2H_5$ C= | 91 – 92 |
| 47 | $CH_3-C(CH_3)_2-CH_2-C(CH_3)=$ | 91 – 92 |
| 48 | $CH_3-CH(CH_3)-CH_2-C(CH_3)=$ | 36 – 37 |
| 49 | $CH_3-CH(CH_3)-(CH_2)_2-C(CH_3)=$ | 56 – 58 |
| 50 | pyridin-4-yl-CH= | 177 – 178 (decomp.) |
| 51 | pyridin-3-yl-CH= | 161 – 163 |
| 52 | pyridin-2-yl-CH= | 136 – 138 |
| 53 | $CH_3-C(CH_3)=CH-C(CH_3)=$ | 130 – 131 |
| 54 | Ph-CH=CH-C(CH_3)= | 136 – 142 |
| 55 | Ph-CHBr-CHBr-C(CH_3)= | 183 – 184 (decomp.) |
| 56 | (Ph)(Ph)C= (fluorenylidene) | 214 – 215 |
| 57 | 3-$NO_2$-C_6H_4-CH= | 185 – 186 |
| 58 | 4-$O_2N$-C_6H_4-CH= | 210 – 211 |
| 59 | Ph-CH=CH-CH= | 187 – 189 |
| 60 | $O=$, $CH_3$ cyclohexadienone C= | 155 – 156 |
| 61 | $CH_3-CH=$ | 95 – 96.5 |
| 61a | 3-Cl-4-HO-5-Cl-C_6H_2-C= | 194 – 195 (decomp.) |

Table 2

| Compound No. | $R_1R_2C=$ | Melting Point °C |
|---|---|---|
| 62 | 4-[(CH_3)_2CH]-C_6H_4-CH= | 130 – 131 |
| 63 | $(CH_3)(CH_3)C=$ | 92 – 94 |
| 64 | C_6H_5-CH= (phenyl CH=) | 85 – 87 |
| 65 | 3-$CH_3O$-4-$OCH_3$-C_6H_3-CH= | 168 – 169 |
| 66 | $C_2H_5-C(CH_3)=$ | 72 – 74 |
| 67 | 2,6-Cl_2-C_6H_3-CH= | 186 – 187 (decomp.) |
| 68 | bicyclic camphor-like C= | 126 – 127 |
| 69 | 2-$OCH_3$-C_6H_4-CH= | 175 – 176 |
| 70 | 3-$C_2H_5O$-4-$OCH_3$-C_6H_3-CH= | 169 – 170 |
| 71 | 2-Cl-C_6H_4-CH= | 182 – 183 |
| 72 | 4-Cl-C_6H_4-CH= | 202 – 203 |
| 73 | $CH_3-CH(CH(CH_3)_2)-C(CH_3)=$ | 68 – 69 |
| 74 | bicyclic terpene-like C= | 110 – 112 |
| 75 | bicyclic terpene-like C= | 104 – 105 |

Table 2-continued

| Compound No. | R₁\C=/R₂ | Melting point °C |
|---|---|---|
| 76 | CH₃—(CH₂)₆—C(CH₃)= | brown oil |
| 77 | C₆H₅—CH= | 165 – 166 |
| 78 | Cl-(NO₂)C₆H₃—CH= | 181 – 183 |
| 79 | CH₃—C(CH₃)=CH—C(CH₃)= | brown oil |
| 80 | CH₃—(CH₂)₃—C(C₂H₅)= | brown oil |
| 81 | C₆H₅—CH=CH—C(CH₃)= | 155 – 165 |
| 82 | C₂H₅—CH(CH₃)—CH₂—C(C₂H₅)= | brown oil |
| 83 | 2-pyridyl-CH= | 128 – 131 |
| 84 | 3-pyridyl-CH= | 132 – 133 |
| 85 | 4-pyridyl-CH= | 148 – 149 |
| 86 | CH₃—CH(CH₃)—CH₂—C(CH₃)= | brown oil |
| 87 | C₆H₅—CHBr—CHBr—C(CH₃)= | 186 – 187 |
| 88 | fluorenylidene | 214 – 215 |
| 88 a | 3,5-diCl-4-HO-C₆H₂—CH= | 194 – 196 (decomp.) |
| 88 b | 3,5-diBr-4-HO-C₆H₂—CH= | 187 – 189 (decomp.) |
| 88 c | 3,5-diI-4-HO-C₆H₂—CH= | 176 – 178 (decomp.) |

The following oxime ethers of 2-nitro-4-carbomethoxyphenol were prepared by methods analogous to those described in the foregoing Examples:

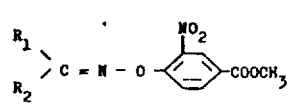

Table 3

| Compound No. | R₁\C=/R₂ | Melting point °C |
|---|---|---|
| 89 | C₆H₅—CH= | 68 – 69 |
| 90 | 2-OCH₃-C₆H₄—CH= | 135 – 137 |
| 91 | 4-Cl-C₆H₄—CH= | 134 – 136 |
| 92 | 2,4-diCl-C₆H₃—CH= | 169 – 171 |
| 93 | 3,5-diI-4-HO-C₆H₂—CH= | 185 – 186 |
| 94 | C₂H₅—C(CH₃)= | 68 – 69 |
| 95 | C₃H₇—C(C₂H₅)= | brown oil |
| 96 | (CH₃)₂CH—CH(C₆H₄)—CH= | 143 – 144 |
| 96 a | 3,5-diCl-4-HO-C₆H₂—CH= | 175 – 176 (decomp.) |
| 96 b | 3,5-diBr-4-HO-C₆H₂—CH= | 181 – 182 (decomp.) |

The following oxime ethers of 2,4-dinitro-6-carbomethoxyphenol were prepared in a similar manner:

$$R_1R_2C=N-O-C_6H_2(NO_2)_2(COOCH_3)$$

Table 4

| Compound No. | R₁\C=/R₂ | Melting point °C |
|---|---|---|
| 97 | 4-Cl-C₆H₄—CH= | 124 – 126 |
| 98 | C₆H₅—CH= | 50 – 51 |
| 99 | 2,4-diCl-C₆H₃—CH= | 105 – 107 |
| 100 | 2-Cl-C₆H₄—CH= | 123 – 124 |
| 101 | 2-OCH₃-C₆H₄—CH= | 133 – 135 |

Table 4-continued

| Compound No. | $R_1R_2C=$ | Melting point °C |
|---|---|---|
| 102 | $(CH_3)_2C=$ with extra $CH_3$ (i.e., $(CH_3)_3C-$ attached, structure as shown) | 65 – 67 |
| 103 | $CH_3-C(CH_3)_2-C(CH_3)=$ | brown oil |
| 104 | $CH_3-CH(CH_3)-CH_2-C(CH_3)=$ | brown oil |
| 105 | $C_6H_5-CH=CH-C(CH_3)=$ | 141 – 143 |
| 106 | 2-pyridyl-CH= | 119 – 120 |
| 107 | 3-pyridyl-CH= | 121 – 122 |
| 108 | 4-pyridyl-CH= | 131 – 132 |
| 109 | 2-Cl-5-$NO_2$-$C_6H_3$-CH= | 156 – 157 |
| 110 | $CH_3-(CH_2)_3-C(C_2H_5)=$ | brown oil |
| 111 | $CH_3-CH(CH_3)-(CH_2)_2-C(CH_3)=$ | brown oil |
| 112 | $C_2H_5-C(C_2H_5)=$ | brown oil |
| 113 | $C_6H_5-CH=CH-C(CH_3)=$ | 141 – 143 |
| 114 | $C_2H_5-CH(CH_3)-CH_2-C(C_2H_5)=$ | brown oil |
| 114 a | 3,5-dibromo-4-hydroxyphenyl-CH= | 165 – 167 |

The following oxime ethers of 2,4-dinitro-6-carboxyclorexoxy were prepared in a similar matter:

Table 5

| Compound No. | $R_1R_2C=$ | Melting point °C |
|---|---|---|
| 115 | 3,4-dichlorophenyl-CH= | 130 – 132 |
| 116 | 4-isopropylphenyl-CH= | 122 – 123 |
| 117 | phenyl-CH= | 111 – 113 |
| 118 | $CH_3-C(OH)(CH_3)-CH_2-C(CH_3)=$ | brown oil |
| 119 | $(C_2H_5)_2C=$ | brown oil |
| 120 | $C_2H_5-C(CH_3)=$ | 75 – 76 |

Furthermore, the following oxime ethers of 2-nitro-4-formylphenol were prepared analogously:

Table 6

| Compound No. | $R_1R_2C=$ | Melting point °C |
|---|---|---|
| 121 | 3,5-diiodo-4-hydroxyphenyl-CH= | 197 – 198 |
| 122 | 4-chlorophenyl-CH= | 143 – 144 |
| 122 a | 3,5-dibromo-4-hydroxyphenyl-CH= | 190 – 191 (decomp.) |

Furthermore, the following oxime ethers of 2-nitro-4-trifluoromethylphenol were prepared analogously:

Table 7

| Compound No. | $R_1R_2C=$ | Melting point °C |
|---|---|---|
| 123 | 3-methoxy-4-ethoxyphenyl-CH= | 143 – 144 |

Table 7-continued

| Compound No. | R₁\C=/R₂ | Melting point °C |
|---|---|---|
| 124 | (bicyclic structure with CH₃, CH₂, CH groups) | 83 – 85 |
| 124 a | HO-C₆H₂(Br)₂-CH= | 149 – 151 (decomp.) |
| 124 b | HO-C₆H₂(I)₂-CH= | 182 – 183 (decomp.) |

The 2,6-dinitro-4-trifluoromethylphenyl ether of the acetonoxime (compound No. 125) melts at 80° – 81°C.

Furthermore, the following oxime ethers of 2,4,6-trinitrophenol were manufactured analogously:

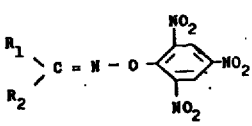

| Compound No. | R₁\C=/R₂ | Melting point °C |
|---|---|---|
| 126 | $\langle H \rangle$ | 164 – 165 |
| 127 | CH₃\C=/CH₃ | 114 – 115 |
| 128 | (Cl, NO₂ phenyl)-CH= | 147 – 148 |
| 129 | CH₃\/CH₃ HC-⟨⟩-CH= | 157 – 158 |

The following oxime ethers of 2-nitro-4-N,N-dimethylsulphamylphenol were manufactured analogously:

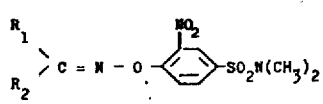

Table 8

| Compound No. | R₁\C=/R₂ | Melting point °C |
|---|---|---|
| 130 | HO-C₆H₂(Br)₂-CH= | 183 – 184 |
| 131 | HO-C₆H₂(I)₂-CH= | 174 – 176 |
| 132 | (bicyclic structure with CH₃, CH₂, CH groups) | 142 – 144 |
| 133 | CH₃-CH-C=/CH₃ CH₃ | 111 – 113 |
| 133 a | HO-C₆H₂(Cl)₂-CH= | 184 – 185 (decomp.) |

The cyclohexanone oxime-2-nitro-4-N-methylsulphamylphenyl ether (compound 134) melts at 129° – 130°C.

Furthermore, the following oxime ethers of 2,4-dinitro-5-aminophenol were manufactured analogously:

Table 9

| Compound No. | R₁\C=/R₂ | Melting point °C |
|---|---|---|
| 135 | ⟨H⟩ | 210 (decomp.) |
| 136 | (C₂H₅)₂N-⟨⟩-CH= | 149 – 150 |
| 137 | CH₃-CH-C=/CH₃ CH₃ | 199 – 200 |
| 138 | CH₃-CH-(CH₂)₂-C=/CH₃ CH₃ | 113 – 114 |
| 139 | cyclohexylidene | 187 – 188 |
| 140 | OCH₃-⟨⟩-CH= | 158 (decomp.) |

The following oxime ethers of 2,4-dinitro-5-isopropylaminophenol were manufactured analogously:

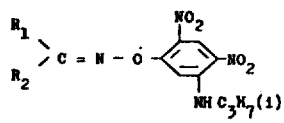

Table 10
| Compound No. | $R_1\diagdown_{C=}\diagup R_2$ | Melting point °C |
|---|---|---|
| 141 |  | 146 – 147 |
Table 10-continued
| Compound No. | | Melting point °C |
|---|---|---|
| 142 | 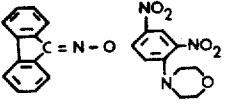 | 159 – 160 |
The following oxime ethers were also manufactured in an analogous way to that described above
| Compound No. | Formula | Melting point °C |
|---|---|---|
| 143 | 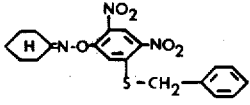 | 229 – 230 (decomp.) |
| 144 | 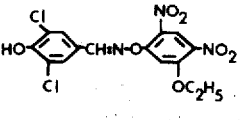 | 133 – 135 |
| 145 | 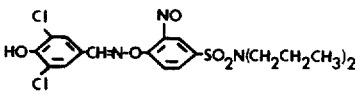 | 197 – 199 (decomp.) |
| 146 | 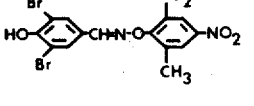 | 157 – 158 (decomp.) |
| 147 | 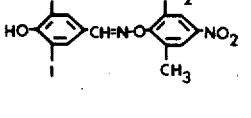 | 157 – 158 (decomp.) |
| 148 | 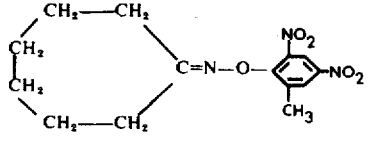 | 160 – 161 (decomp.) |
| 149 | 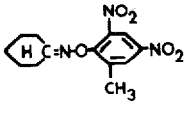 | Oil |
| 150 | 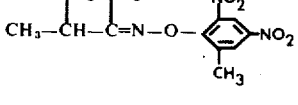 | 81 – 83 |
| 151 | $CH_3-CH-CH-C=N-O-$ ... | 58 – 59 |

-continued
| Compound No. | Formula | Melting point °C |
|---|---|---|
| 152 | 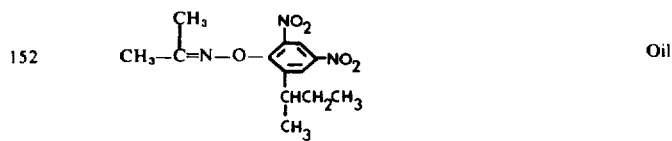 | Oil |
| 153 | 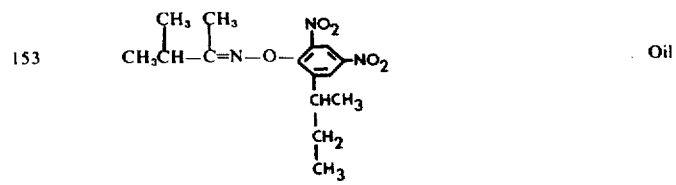 | Oil |
| 154 | 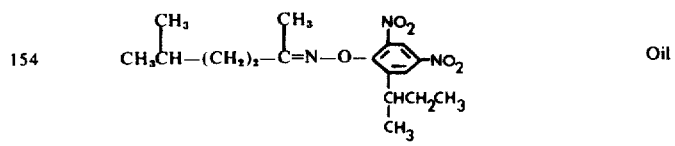 | Oil |
| 155 | 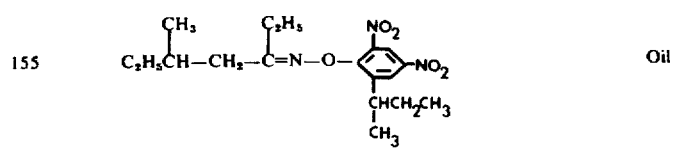 | Oil |
| 156 | 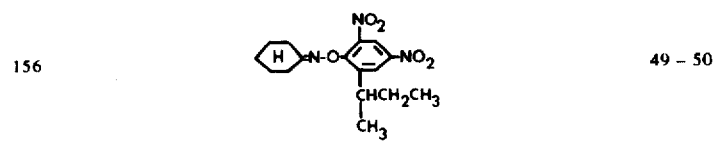 | 49 – 50 |
| 157 | 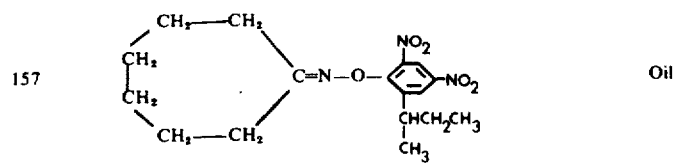 | Oil |
| 158 | 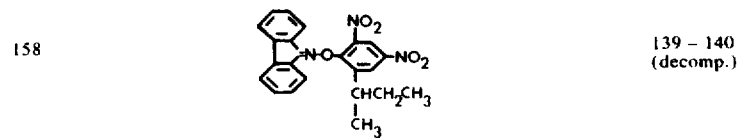 | 139 – 140 (decomp.) |
| 159 | 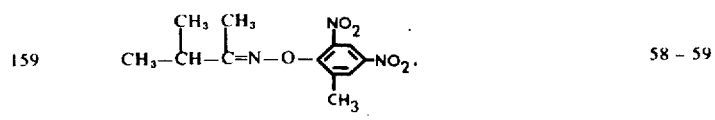 | 58 – 59 |

| Compound No. | Formula | Melting point °C |
|---|---|---|
| 160 | 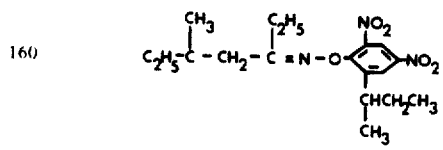 | Oil |
| 161 | 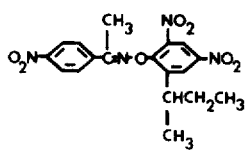 | 92 – 93 |
| 162 | 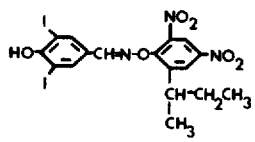 | 136 – 137 (decomp.) |

EXAMPLE 13 a. A mixture of 50 g of the active ingredient No. 14, 20 g of Hisil (a silica preparation), 25 g of kaolin, 3.5 g of flotation agent (for example a condensation product of 1 mol of para-octylphenol with 6 to 10 mols of ethylene oxide) and 1.5 g of a wetting agent (for example the sodium salt of 1-benzyl-2-heptadecylbenzimidazole-disulphonic acid) is finely ground to form a wettable powder containing 50% of the active product.

The active ingredient No. 21 is formulated in a similar manner, except that 25 g of chalk are used instead of 25 g of kaolin. In an identical manner, the active substance No. 14 of Example 4 is formulated.

b. 500 Grams each of the active ingredients Nos. 5 and 67 are mixed with 110 g of ammonium ligninsulphonate, 45 g of dicresyl methanedisulphonic acid, 10 g of a mixture of 40% of an alkylarylpolyether alcohol and 60% of magnesium carbonate, and 335 g of kaolin. In each case, the resulting mixture may be diluted with water to form a stable emulsion.

EXAMPLE 14 a. When used for a postemergence treatment, the following active compounds produced a good effect against a variety of dicotyledonous plants.

The above mentioned treatment was carried out with 5.0 kg each of the active compounds listed below 12 days after sowing, when the plants had developed 1 to 2 genuine leaves.

The following results were recorded:

| Species of plant | Comp. No. 1 | No. 2 | No. 13 | No. 14 | No. 15 | No. 17 | No. 18 | No. 19 | No. 21 | No. 26 | No. 27 | No. 29 |
|---|---|---|---|---|---|---|---|---|---|---|---|---|
| Beta vulgaris | 9 | 9 | 9 | 9 | 9 | 10 | 10 | 9 | 10 | 10 | 10 | 10 |
| Calendula | 9 | 10 | 10 | 10 | 10 | 10 | 10 | 10 | 8 | 10 | 10 | 10 |
| Linum | 10 | 8 | 8 | 10 | 10 | 10 | 10 | 10 | 8 | 10 | 10 | 9 |
| Brassica | 9 | 10 | 10 | 10 | 9 | 10 | 10 | 9 | 10 | 10 | 10 | 10 |
| Daucus | 9 | 10 | 10 | 9 | 2 | 8 | 10 | 10 | 8 | 9 | 8 | 10 |
| Lactuca | 10 | 10 | 10 | 10 | 2 | 5 | 10 | 10 | 10 | 10 | 10 | 2 |
| Medicago | 2 | 4 | 4 | 10 | 6 | 10 | 10 | 9 | 10 | 10 | 10 | 2 |
| Soya | 1 | 2 | 9 | 10 | 1 | 4 | 8 | 7 | 8 | 4 | 1 | 10 |
| Triticum | 0 | 0 | 0 | 1 | 0 | 0 | 0 | 0 | 0 | 1 | 1 | 1 |
| Hordeum | 2 | 1 | 2 | 0 | 2 | 3 | 3 | 2 | 1 | 3 | 2 | 1 |
| Sorghum | 1 | 1 | 0 | 1 | 1 | 2 | 4 | 1 | 2 | 2 | 1 | 1 |
| Phaseolus | 4 | 9 | 5 | 4 | 2 | 6 | 5 | 9 | 7 | 4 | 5 | 1 |

| Species of plant | Comp. No. 32 | No. 33 | No. 36 | No. 37 | No. 41 | No. 43 | No. 46 | No. 47 | No. 56 | No. 62 | No. 65 |
|---|---|---|---|---|---|---|---|---|---|---|---|
| Beta vulgaris | 9 | 8 | 10 | 10 | 10 | 10 | 10 | 10 | 10 | 10 | 10 |
| Calendula | 8 | 7 | 10 | 9 | 10 | 10 | 10 | 10 | 8 | 10 | 10 |
| Linum | 10 | 7 | 10 | 10 | 10 | 8 | 9 | 9 | 7 | 10 | 10 |
| Brassica | 10 | 8 | 10 | 10 | 10 | 10 | 10 | 10 | 10 | 10 | 10 |
| Daucus | 10 | 6 | 10 | 9 | 9 | 8 | 8 | 10 | 8 | 8 | 6 |
| Lactuca | 8 | 5 | 10 | 9 | 10 | 10 | 10 | 10 | 9 | 8 | 8 |
| Medicago | 2 | 2 | 2 | 3 | 6 | 10 | 10 | 10 | 6 | 8 | 9 |
| Soya | 0 | 0 | 0 | 0 | 0 | 8 | 1 | 1 | 6 | 1 | 1 |
| Triticum | 0 | 0 | 0 | 0 | 0 | 0 | 1 | 0 | 0 | 0 | 0 |
| Hordeum | 2 | 1 | 1 | 1 | 0 | 0 | 1 | 0 | 0 | 0 | 1 |
| Sorghum | 1 | 1 | 2 | 2 | 1 | 0 | 0 | 1 | 0 | 0 | 4 |
| Phaseolus | 4 | 7 | 8 | 4 | 5 | 8 | 4 | 2 | 4 | 1 | 4 |

| Species of plant | No. 71 | No. 72 | No. 88 | No. 91 | No. 92 | No. 93 | No. 97 | No. 98 | No. 100 | No. 101 | No. 109 | No. 121 | No. 130 | No. 131 |
|---|---|---|---|---|---|---|---|---|---|---|---|---|---|---|
| Beta vulgaris | 10 | 10 | 10 | 8 | 8 | 10 | 8 | 10 | 10 | 10 | 10 | 8 | 10 | 8 |
| Calendula | 10 | 10 | 10 | 8 | 10 | 10 | 10 | 10 | 10 | 10 | 8 | 7 | 8 | 10 |
| Linum | 10 | 10 | 10 | 8 | 10 | 8 | 10 | 10 | 10 | 10 | 8 | 8 | 10 | 10 |
| Brassica | 10 | 8 | 10 | 10 | 10 | 8 | 8 | 10 | 10 | 8 | 8 | 10 | 8 | 6 |
| Daucus | 6 | 10 | 10 | 9 | 5 | 10 | 8 | 10 | 10 | 8 | 8 | 10 | 10 | 10 |
| Lactuca | 8 | 10 | 10 | 9 | 10 | 8 | 5 | 10 | 8 | 10 | 10 | 9 | 10 | 8 |
| Medicago | 10 | 8 | 10 | 6 | 10 | 10 | 10 | 10 | 8 | 10 | 8 | 10 | 8 | 10 |
| Soya | 1 | 1 | 1 | 5 | 8 | 10 | 8 | 1 | 1 | 8 | 8 | 2 | 10 | 10 |
| Triticum | 0 | 0 | 1 | 0 | 1 | 0 | 1 | 1 | 1 | 0 | 0 | 0 | 0 | 0 |
| Hordeum | 0 | 0 | 0 | 1 | 0 | 0 | 0 | 1 | 0 | 1 | 1 | 1 | 1 | 1 |
| Sorghum | 2 | 2 | 1 | 0 | 1 | 0 | 1 | 0 | 1 | 0 | 0 | 0 | 1 | 1 |
| Phaseolus | 8 | 6 | 7 | 5 | 4 | 7 | 8 | 8 | 5 | 10 | 10 | 6 | 4 | 5 |

Explanation:
0 = no effect
<5 = damage that spreads
>5 = damage that results in the plant dying off
10 = plant completely destroyed.

Each of the active compounds Nos. 5, 10, 20, 56, 67, 88 and 99, formulated as described in Example 13b was sprayed on the soil in an amount of 0.5 kg per hectare, in a greenhouse test immediately after sowing — i.e. by the preemergence method. The test plants and the results achieved are listed in the following Table:

| Species of plant | Comp. No. 5 | No. 10 | No. 20 | No. 56 | No. 67 | No. 88 | No. 99 |
|---|---|---|---|---|---|---|---|
| Triticum | 2 | 2 | 2 | 2 | 2 | 1 | 1 |
| Hordeum | 2 | 2 | 1 | 1 | 2 | 2 | 1 |
| Avena | 10 | 8 | 8 | 8 | 8 | 10 | 8 |
| Poa | 10 | 10 | 10 | 10 | 10 | 10 | 8 |
| Dactylis | 10 | 10 | 10 | 10 | 10 | 10 | 10 |
| Linum | 3 | 3 | 5 | 5 | 3 | 5 | 10 |
| Brassica | 3 | 3 | 2 | 2 | 1 | 0 | 0 |
| Lactuca | 10 | 8 | 8 | 10 | 10 | 10 | 10 |
| Medicago | 4 | 5 | 8 | 8 | 8 | 10 | 8 |
| Soya | 1 | 1 | 1 | 1 | 1 | 0 | 0 |
| Phaseolus | 1 | 1 | 0 | 1 | 0 | 1 | 0 |

0 = no effect
10 = plant completely destroyed

When applied in an amount of 0.5 kg of active compound only a few plants were strongly affected, above all Avena, Poa, Dactylis and Lactuca, whereas the others were not damaged at all or only to a very small extent, such as Triticum, Hordeum, Brassica, Soya and Phaseolus.

b. The active substances Nos. 5 and 67, formulated as described in Example 13b, in an amount of 4.0, 2.0, 1.0 and 0.5 kg of active substance per hectare, were sprayed over the soil in a greenhouse test immediately after seeding, that is to say, by the pre-emergence method. The seedlings treated and the results achieved are shown in the following Table:

| | Active substance No. 5 | | | | Active substance No. 67 | | | |
|---|---|---|---|---|---|---|---|---|
| | 4 | 2 | 1 | 0.5 kgAS | 4 | 2 | 1 | 0.5 kgAS |
| Triticum | 10 | 10 | 9 | 2 | 10 | 7 | 7 | 2 |
| Hordeum | 10 | 5 | 5 | 2 | 10 | 4 | 5 | 2 |
| Avena | 10 | 10 | 10 | 10 | 10 | 10 | 10 | 8 |
| Poa | 10 | 10 | 10 | 10 | 10 | 10 | 10 | 10 |
| Dactylis | 10 | 10 | 10 | 10 | 10 | 10 | 10 | 10 |
| Linum | 10 | 10 | 10 | 3 | 10 | 9 | 8 | 3 |
| Brassica | 10 | 10 | 5 | 3 | 10 | 4 | 2 | 1 |
| Lactuca | 10 | 10 | 10 | 10 | 10 | 10 | 10 | 10 |
| Medicago | 10 | 10 | 10 | 4 | 10 | 10 | 10 | 8 |
| Soya | 10 | 7 | 4 | 1 | 9 | 4 | 2 | 1 |
| Phaseolus | 5 | 1 | 1 | 1 | 4 | 1 | 0 | 0 |

0 = no effect
10 = plant completely destroyed

When applied in an amount of 4.0 kg per hectare both these products of the invention displayed a broad effect, whereas with 0.5 kg of active substance only some plants were strongly effected, above all Avena, Poa, Dactylis and Lactuca, whereas others were not damaged at all or only very little, for example Triticum, Hordeum, Brassica, Soya and Phaseolus.

Accordingly, the two new active substances may be used as total herbicides by the pre-emergence method or, when used in a suitable concentration, for the selective control of weeds, for example in grain crops (Triticum and Hordeum), varieties of cabbage (Brassica) and leguminoses (soybeans and phaseolus beans).

EXAMPLE 15

Mixtures containing 50 g of the active substances Nos. 16, 20, 22, 4 and 66 each, 3.5 g of a non-ionic, and 1.5 g of an anionic wetting and dispersing agent are finely ground with 50 g of a vehicle. The wettable spray powders thus obtained may be diluted with water in any desired proportion.

EXAMPLE 16

10 to 40 Grams of each of the compounds 68, 73, 75, 98 76 and 94 are made up with an adequate amount of an emulsifier (sulphonate-nonionic mixture) in xylene to a volume of 100 ml. These emulsion concentrates may be diluted with water to the desired concentration and used as fungicides.

EXAMPLE 17

The products of this invention, for example compound No. 16, are also distinguished by their action against genuine powdery mildew. Zucchetti plants (Cucumis pepo) were trained in a greenhouse and once sprayed prophylactically with a broth containing as active ingredient 0.2% of the preparation formulated as described in Example 15. 2 Days after having been sprayed, the plants were infested with spores of Erysiphe cichoracearum and 12 to 14 days later checked for fungus attack. Compared with the untreated control (effect: nil) the sprayed plants displayed a 90% effect without having developed phytotoxic damage.

Effects similar to those against Erysiphe cichoracearum described above were observed with the following compounds, which were readily tolerated by the Zucchetti plants:

| Compound No. | Effect in % |
|---|---|
| 20 | 80 |
| 4 | 100 |
| 49 | 95 |
| 66 | 80 |

EXAMPLE 18

The action of the compounds of this invention against leaf spot fungi was confirmed on celery (Apium graveolens) with the fungus Septoria apii. Celery plants were trained in a greenhouse and, 2 days before infection with the fungus Septoria, sprayed with broths each containing 0.2% of one of the active compounds mentioned below. After infection, the plants were placed for 2 to 3 weeks in an incubation room having a high atmospheric humidity and then checked for infestation against an untreated control series, which latter revealed a nil-return. The effects produced by the compounds of this invention are listed in the following Table:

| Compound No. | Effect in % |
|---|---|
| 20 | 93 |
| 22 | 80 |
| 4 | 93 |
| 66 | 100 |
| 68 | 94 |
| 73 | 100 |
| 75 | 95 |
| 98 | 94 |
| 76 | 100 |
| 94 | 87 |
| 80 | 100 |

EXAMPLE 19

Herbicidal effect in the greenhouse

|  | Preemergent compound No. 99 | | | Postemergent compound No. 93 | |
|---|---|---|---|---|---|
| KgAS | 2.0 | 1.0 | 0.5 | 0.25 | 5.0 | 2.5 |
| Triticum | 10 | 10 | 9 | 7 | 0 | 0 |
| Hordeum | 10 | 9 | 7 | 4 | 0 | 0 |
| Avena | 10 | 10 | 10 | 10 | 1 | 1 |
| Sorghum | 8 | 4 | 2 | 1 | 2 | 1 |
| Panicum | 10 | 10 | 8 | 1 | 10 | 8 |
| Poa | 10 | 10 | 10 | 8 | 6 | 2 |
| Dactylis | 10 | 10 | 10 | 10 | 4 | 2 |
| Digitaria | 10 | 10 | 4 | 1 | 7 | 4 |
| Beta | 10 | 10 | 10 | 10 | 10 | 10 |
| Calendula | 10 | 10 | 10 | 10 | 10 | 10 |
| Linum | 10 | 10 | 10 | 5 | 10 | 10 |
| Brassica | 10 | 10 | 7 | 8 | 10 | 10 |
| Daucus | 10 | 10 | 10 | 10 | 10 | 10 |
| Lactuca | 10 | 10 | 10 | 10 | 10 | 10 |
| Soya | 10 | 8 | 2 | 0 | 4 | 3 |
| Phaseolus | 10 | 10 | 1 | 0 | 8 | 5 |

When compound No. 99 was applied in an amount of 2 kg or over, it displayed total herbicidal properties.

When a small amount, for example 0.25 kg, of the active substance of this invention is applied, numerous test plants can be completely or almost completely destroyed without affecting, for example, soybean or phaseolus bean plants. With even smaller amounts wild oats (Avena fatua) in barley (Hordeum) may be controlled.

Compound No. 93, applied in an amount of 2.5 kg, was successfully applied against numerous dicotyledons and Panicum, whereas the various types of grain crops were not damaged by the active substance of the invention.

EXAMPLE 20

Test on Grain Crops in the Field

In a field of winter wheat which had just been tilled and in which the weeds had reached the 4-leaf stage, the compounds Nos. 18 and 26 were sprayed in an amount of 8.0 kg per hectare. 3 Weeks after the treatment, the effects achieved on weeds were found to be very good (that is to say value 1 and 2 respectively). Grain crops, on the other hand, had not been damaged (value 1–2).

Test on salad in the open

The compound No. 27 was sprayed in an amount of 8.0 kg per hectare on salad four weeks after seeding (3–4 leaf stage) and when the weeds had reached the stage of the large rosette.

The effect achieved on the weeds was good (value 3), whereas the salad was not affected by the herbicide of this invention.

Tests with marrow cabbage in the open

Immediately after seeding marrow cabbage and before the weeds had emerged, the soil surface was sprayed with the compounds Nos. 5 and 67 of this invention each being used in amounts of 2.0, 3.0 and 4.0 kg per hectare. The effect achieved and the tolerance observed are shown in the Table, where the following values are used: For effect on weeds 1 = very good, 9 = effect nil. For tolerance by culture plants: 1 = very good, 9 = total destruction.

| Amount used kg AS/ha | Compound No. 5 | | | Compound No. 67 | |
|---|---|---|---|---|---|
| | 2.0 | 3.0 | 4.0 | 3.0 | 4.0 |
| effect on weeds | 3 | 3 | 2 | 2 | 2 |
| tolerance by culture plants | 2 | 2 | 2 | 3 | 5 |

EXAMPLE 21

All compounds to be tested were formulated in the usual manner.

To check their acaricidal effect, Phaseolus plants in the 2-leaf stage were infested 12 hours before the treatment by covering them with pieces of leaves infested by a mite species (Tetranychus telarius or Tetranychus urticae; carmine red mite). 12 Hours later, the test plant was found to be covered with mites in all stages of development. The active ingredient, in the form of an emulsion, was sprayed with the aid of a fine sprayer over the plants in a manner such that a uniform layer of droplets was formed on the leaf surface. The mortality was checked 2 and 7 days later and expressed in percent. The effect upon ova cannot be stated after the test had been run for 2 days as described because the average time taken by the larvae to leave the ova has not yet been established.

At a concentration of 0.08% of active ingredient the following mortality values were found:

| Comp. No. | | Ova | Larvae | Adults |
|---|---|---|---|---|
| 1 | After 2 days | — | 100% | 100% |
| | After 7 days | 100% | 100% | 100% |
| 2 | After 2 days | — | 100% | 100% |
| | After 7 days | 100% | 100% | 100% |
| 3 | After 2 days | — | 100% | 100% |
| | After 7 days | 100% | 100% | 100% |
| 4 | After 2 days | — | 100% | 100% |
| | After 7 days | 100% | 100% | 100% |
| 5 | After 2 days | — | 100% | 100% |
| | After 7 days | 100% | 100% | 100% |
| 13 | After 2 days | — | 100% | 100% |
| | After 7 days | 80% | 100% | 100% |
| 14 | After 2 days | — | 100% | 100% |
| | After 7 days | 100% | 100% | 100% |
| 15 | After 2 days | — | 100% | 100% |
| | After 7 days | 90% | 100% | 100% |
| 29 | After 2 days | — | 100% | 100% |
| | After 7 days | 100% | 100% | 100% |
| 31 | After 2 days | — | 100% | 100% |
| | After 7 days | 80% | 100% | 100% |
| 45 | After 2 days | — | 100% | 100% |
| | After 7 days | 80% | 100% | 100% |
| 46 | After 2 days | — | 100% | 100% |
| | After 7 days | 100% | 100% | 100% |
| 58 | After 2 days | — | 100% | 100% |
| | After 7 days | 80% | 100% | 100% |
| 72 | After 2 days | — | 100% | 100% |
| | After 7 days | 80% | 100% | 100% |
| 78 | After 2 days | — | 100% | 100% |
| | After 7 days | 100% | 100% | 100% |
| 91 | After 2 days | — | 100% | 100% |
| | After 7 days | 100% | 100% | 100% |
| 101 | After 2 days | — | 100% | 100% |
| | After 7 days | 100% | 100% | 100% |
| 115 | After 2 days | — | 100% | 100% |
| | After 7 days | 100% | 100% | 100% |
| 123 | After 2 days | — | 100% | 100% |
| | After 7 days | 100% | 100% | 100% |

Compound No. 4, applied in a concentration of 0.05%, displayed a good killing effect against red spiders, for example against Panonychus ulmi, Eotetranychus tiliae a good killing effect, in fact against both their ova and the postembryonal stages.

The following compounds show at concentrations of 0.05% the following mortality rate (ovicidal effect) against panonychus ulmi. (control after 7 days)

| Compound No. | Mortality rate in % |
|---|---|
| 3 | 95 |
| 9 | 100 |
| 10 | 100 |
| 21 | 100 |
| 56 | 100 |
| 62 | 80 |
| 78 | 100 |
| 82 | 100 |
| 88 | 100 |
| 95 | 100 |
| 119 | 100 |
| 129 | 100 |

In the following tables also Tetranychus urticae which is resistent to phosphorus acid esters is listed.

Compound No. 153 a. action against *Tetr. urticae*

| | Mortality | | | | |
|---|---|---|---|---|---|
| | after 2 days | | | after 7 days | |
| Conc. (ppm) | Larvae | Adults | Ova | Larvae | Adults |
| 800 | 100 | 100 | 100 | 100 | 100 |
| 400 | 100 | 100 | 100 | 100 | 100 |
| 200 | 100 | 100 | 80 | 80 | 100 |
| 100 | 100 | 100 | 0 | 80 | 80 | b. action against *Tetr. telarius*

| | Mortality | | | | |
|---|---|---|---|---|---|
| | after 2 days | | | after 7 days | |
| Conc. ppm | Larvae | Adults | Ova | Larvae | Adults |
| 800 | 100 | 100 | 100 | 100 | 100 |
| 400 | 100 | 100 | 100 | 100 | 100 |
| 200 | 100 | 100 | 80 | 80 | 100 |
| 100 | 100 | 100 | 0 | 60 | 80 |

Compound No. 154 a. action against *Tetr. urticae*

| | Mortality | | | | |
|---|---|---|---|---|---|
| | after 2 days | | | after 7 days | |
| Conc. ppm | Larvae | Adults | Ova | Larvae | Adults |
| 800 | 100 | 100 | 60 | 100 | 100 |
| 400 | 100 | 100 | 0 | 80 | 100 |
| 200 | 100 | 100 | 0 | 60 | 80 |
| 100 | 100 | 100 | 0 | 0 | 80 | b. Action against *Tetr. telarius*

| | Mortality | | | | |
|---|---|---|---|---|---|
| | after 2 days | | | after 7 days | |
| Conc. ppm | Larvae | Adults | Ova | Larvae | Adults |
| 800 | 100 | 80 | 0 | 100 | 100 |
| 400 | 100 | 80 | 0 | 100 | 100 |
| 200 | 100 | 80 | 0 | 80 | 80 |

Compound No. 155 a. Action against *Tetr. urticae*

| | Mortality | | | | |
|---|---|---|---|---|---|
| | after 2 days | | | after 7 days | |
| Conc. ppm | Larvae | Adults | Ova | Larvae | Adults |
| 800 | 100 | 100 | 60 | 100 | 80 |
| 400 | 100 | 100 | 0 | 80 | 100 |

-continued

Mortality

| Conc. ppm | after 2 days Larvae | Adults | Ova | after 7 days Larvae | Adults |
|---|---|---|---|---|---|
| 200 | 100 | 100 | 0 | 0 | 100 | b. Action against *Tetr. telarius*

Mortality

| Conc. ppm | after 2 days Larvae | Adults | Ova | after 7 days Larvae | Adults |
|---|---|---|---|---|---|
| 800 | 100 | 80 | 0 | 100 | 100 |
| 400 | 100 | 80 | 0 | 80 | 80 |
| 200 | 80 | 80 | 0 | 0 | 80 |

Compound No. 156
a. Action against *Tetr. urticae*

Mortality

| Conc.ppm | after 2 days Larvae | Adults | Ova | after 7 days Larvae | Adults |
|---|---|---|---|---|---|
| 800 | 100 | 100 | 100 | 100 | 100 |
| 400 | 100 | 100 | 100 | 100 | 100 |
| 200 | 100 | 100 | 80 | 100 | 100 |
| 100 | 100 | 100 | 60 | 80 | 100 | b. Action against *Tetr. telarius*

Mortality

| Conc.ppm | after 2 days Larvae | Adults | Ova | after 7 days Larvae | Adults |
|---|---|---|---|---|---|
| 800 | 100 | 100 | 100 | 100 | 100 |
| 400 | 100 | 100 | 100 | 100 | 100 |

Compound No. 157
a. Action against Tetr. urticae

Mortality

| Conc.ppm | after 2 days Larvae | Adults | Ova | after 7 days Larvae | Adults |
|---|---|---|---|---|---|
| 800 | 100 | 100 | 60 | 100 | 100 |
| 400 | 100 | 80 | 80 | 80 | 100 |
| 200 | 80 | 80 | 60 | 80 | 80 |
| 100 | 80 | 60 | 0 | 60 | 60 | b. Action against *Tetr. telarius*

Mortality

| Conc.ppm | after 2 days Larvae | Adults | Ova | after 7 days Larvae | Adults |
|---|---|---|---|---|---|
| 800 | 100 | 80 | 80 | 80 | 100 |
| 400 | 100 | 80 | 80 | 80 | 80 |
| 200 | 80 | 80 | 60 | 60 | 80 |
| 100 | 60 | 0 | 0 | 0 | 60 |

Compound No. 159
a. Action against *Tetr. urticae*

Mortality

| Conc.ppm | after 2 days Larvae | Adults | Ova | after 7 days Larvae | Adults |
|---|---|---|---|---|---|
| 800 | 80 | 80 | 60 | 100 | 100 |
| 400 | 80 | 80 | 60 | 80 | 100 |
| 200 | 80 | 80 | 60 | 60 | 0 |
| 100 | 80 | 80 | 0 | 0 | 0 | b. Action against *Tetr. telarius*

Mortality

| Conc.ppm | after 2 days Larvae | Adults | Ova | after 7 days Larvae | Adults |
|---|---|---|---|---|---|
| 800 | 80 | 80 | 80 | 100 | 100 |
| 400 | 80 | 80 | 80 | 80 | 100 |
| 200 | 80 | 60 | 60 | 60 | 0 |
| 100 | 60 | 0 | 0 | 0 | 0 |

Compound No. 160
a. Action against Tetr. urticae

Mortality

| Conc.ppm | after 2 days Larvae | Adults | Ova | after 7 days Larvae | Adults |
|---|---|---|---|---|---|
| 800 | 100 | 100 | 80 | 100 | 100 |
| 400 | 100 | 100 | 80 | 100 | 100 |
| 200 | 100 | 100 | 80 | 100 | 100 |
| 100 | 100 | 100 | 60 | 80 | 100 | b. Action against *Tetr. telarius*

Mortality

| Conc.ppm | after 2 days Larvae | Adults | Ova | after 7 days Larvae | Adults |
|---|---|---|---|---|---|
| 800 | 100 | 100 | 80 | 100 | 100 |
| 400 | 100 | 100 | 80 | 100 | 100 |
| 200 | 100 | 100 | 60 | 80 | 100 |
| 100 | 100 | 100 | 60 | 80 | 100 |

EXAMPLE 22

Compound No. 4, applied in a concentration of 0.05%, displayed a good killing effect against red spiders, for example against *Panonychus ulmi*, *Eotetranychus tiliae* in fact against both their ova and the postembryonal stages.

Equally good results were observed with compounds Nos. 21 and 3.

EXAMPLE 23

Freshly laid ova of the flour moth *Ephestia Kuehniella* (20 each) were placed in folded paper filters, the emulsified compound No. 36 was poured over them and they were then spread open and allowed to dry at room temperature. When the filter had completely dried, each moth tested was covered with a wire net and kept until the untreated control moth had left its ovum. The checking of the effects was carried out under a binocular microscope and revealed the following total destruction (active substance in parts per million):

| Concentration of active substance in ppm | 1000 | 500 | 250 | 125 | 62.5 |
|---|---|---|---|---|---|
| % killed | 100 | 100 | 100 | 100 | 100 |

I claim:
1. A compound of the formula

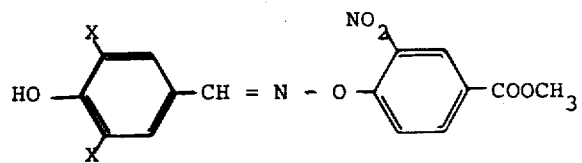
in which X is chlorine, bromine or iodine.
* * * * *